(12) United States Patent
Zheng et al.

(10) Patent No.: US 9,915,658 B2
(45) Date of Patent: Mar. 13, 2018

(54) REAGENTS FOR HCV ANTIGEN-ANTIBODY COMBINATION ASSAYS

(71) Applicant: ORTHO-CLINICAL DIAGNOSTICS, INC., Raritan, NJ (US)

(72) Inventors: Jian Zheng, Raritan, NJ (US); Jianping Yang, Phillipsburg, NJ (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 9 days.

(21) Appl. No.: 14/982,015

(22) Filed: Dec. 29, 2015

(65) Prior Publication Data

US 2016/0109447 A1   Apr. 21, 2016

Related U.S. Application Data

(63) Continuation of application No. 12/469,568, filed on May 20, 2009, now abandoned.

(51) Int. Cl.
| | | |
|---|---|---|
| G01N 33/576 | (2006.01) | |
| G01N 33/569 | (2006.01) | |
| G01N 33/53 | (2006.01) | |

(52) U.S. Cl.
CPC ... *G01N 33/56983* (2013.01); *G01N 33/5306* (2013.01); *G01N 33/5767* (2013.01); *G01N 2333/186* (2013.01); *G01N 2469/10* (2013.01); *G01N 2469/20* (2013.01)

(58) Field of Classification Search
CPC .......... G01N 33/5767; G01N 2469/20; G01N 2469/10; G01N 2333/186
See application file for complete search history.

(56) References Cited

U.S. PATENT DOCUMENTS

| | | | |
|---|---|---|---|
| 4,870,003 A | 9/1989 | Kortright et al. | |
| 5,447,837 A | 9/1995 | Urnovitz | |
| 5,627,026 A | 5/1997 | O'Connor et al. | |
| 5,763,158 A | 6/1998 | Bohannon | |
| 6,171,782 B1 | 1/2001 | Houghton et al. | |
| 6,383,740 B2 | 5/2002 | Collins | |
| 6,538,123 B2 | 3/2003 | Barban | |
| 6,593,079 B1 | 7/2003 | Danie et al. | |
| 6,623,921 B2 * | 9/2003 | Aoyagi .............. | G01N 33/5767 435/5 |
| 6,723,502 B2 | 4/2004 | Bahl et al. | |
| 6,727,092 B2 | 4/2004 | Shah et al. | |
| 6,855,809 B2 | 2/2005 | Shah et al. | |
| 7,101,683 B2 | 9/2006 | Shah et al. | |
| 2002/0037868 A1 | 3/2002 | Budkowska et al. | |
| 2002/0192639 A1 | 12/2002 | Chien et al. | |
| 2003/0049608 A1 | 3/2003 | Bahl et al. | |
| 2003/0108563 A1 | 6/2003 | Bahl | |
| 2003/0152948 A1 | 8/2003 | Shah et al. | |
| 2004/0152070 A1 | 8/2004 | Shah et al. | |

FOREIGN PATENT DOCUMENTS

| | | |
|---|---|---|
| EP | 0 648 228 B1 | 11/1998 |
| EP | 1 251 353 A2 | 10/2002 |
| EP | 1 310 796 A2 | 5/2003 |
| EP | 0 967 484 B1 | 5/2007 |
| JP | 2004-506878 A | 3/2004 |
| WO | 99/58561 A1 | 11/1999 |
| WO | 01/96875 A2 | 12/2001 |
| WO | 03/002749 A2 | 9/2003 |
| WO | 03/095968 A2 | 11/2003 |
| WO | 04/070387 A1 | 8/2004 |

OTHER PUBLICATIONS

Urbani, A., et al., 1999, Multiple determinants influence complex formation of the hepatitis C virus NS3 protease domain with its NS4A cofactor peptide, Biochem. 38:5206-5215.*
Urbani et al. Multiple determinants influence complex formation of the Hepatitis C virus NS3 protease domain with its NS4A cofactor peptide. Biochemistry 1999, vol. 38, pp. 5206-5215.
Shah et al., "Combination HCV core antigen and antibody assay on a fully automated chemiluminescence analyzer", Transfusion 43(8):1067-1074 (Aug. 2003).
Tuke et al., "Hepatitis C virus window-phase infections: closing the window on hepatitis C virus", Transfusion 48(4):594-600 (Apr. 2008).
Korean Office Action dated Mar. 28, 2017 received in corresponding Korean Patent Application No. 10-2010-0047432.

* cited by examiner

*Primary Examiner* — Jeffrey Parkin
(74) *Attorney, Agent, or Firm* — Scully Scott Murphy & Presser

(57) ABSTRACT

The present invention is directed to combination immunoassays, reagents and kits for simultaneous detection of HCV antigens and anti-HCV antibodies in a sample. The combination immunoassays of the present invention employ a non-ionic detergent that effectively exposes or releases the HCV core antigen from virions in a sample without interfering with the performance of other reagents such as the capture of anti-HCV antibodies by recombinant HCV antigens.

10 Claims, No Drawings

SEQUENCE LISTING

```
<160> NUMBER OF SEQ ID NOS: 3

<210> SEQ ID NO 1
<211> LENGTH: 38
<212> TYPE: PRT
<213> ORGANISM: Artificial
<220> FEATURE:
<223> OTHER INFORMATION: Synthetic HCV antigenic peptide "HCC5N"
<220> FEATURE:
<221> NAME/KEY: MOD_RES
<222> LOCATION: (37)..(37)
<223> OTHER INFORMATION: Nle

<400> SEQUENCE: 1

Lys Thr Lys Arg Asn Thr Asn Arg Arg Pro Gln Asp Val Lys Phe Pro
1               5                   10                  15

Gly Gly Gly Gln Ile Val Gly Val Tyr Leu Leu Pro Arg Arg Gly
            20                  25                  30

Pro Arg Leu Gly Xaa Cys
            35

<210> SEQ ID NO 2
<211> LENGTH: 38
<212> TYPE: PRT
```

```
<213> ORGANISM: Artificial
<220> FEATURE:
<223> OTHER INFORMATION: Synthetic HCV antigenic peptide "HCC5-b"
<220> FEATURE:
<221> NAME/KEY: MISC_FEATURE
<222> LOCATION: (38)..(38)
<223> OTHER INFORMATION: Xaa is biotinylated Lysine

<400> SEQUENCE: 2

Lys Thr Lys Arg Asn Thr Asn Arg Arg Pro Gln Asp Val Lys Phe Pro
1               5                   10                  15

Gly Gly Gly Gln Ile Val Gly Val Tyr Leu Leu Pro Arg Arg Gly
            20                  25                  30

Pro Arg Leu Gly Gly Xaa
            35

<210> SEQ ID NO 3
<211> LENGTH: 462
<212> TYPE: PRT
<213> ORGANISM: Artificial
<220> FEATURE:
<223> OTHER INFORMATION: Recombinant fusion protein between 6xHis tag
      and HCV rNS3(h)
<220> FEATURE:
<221> NAME/KEY: MISC_FEATURE
<222> LOCATION: (1)..(12)
<223> OTHER INFORMATION: 6xHis tag

<400> SEQUENCE: 3

Met Arg Gly Ser His His His His His His Gly Ser Pro Val Phe Thr
1               5                   10                  15

Asp Asn Ser Ser Pro Pro Val Val Pro Gln Ser Phe Gln Val Ala His
            20                  25                  30

Leu His Ala Pro Thr Gly Ser Gly Lys Ser Thr Lys Val Pro Ala Ala
        35                  40                  45

Tyr Ala Ala Gln Gly Tyr Lys Val Leu Val Leu Asn Pro Ser Val Ala
    50                  55                  60

Ala Thr Leu Gly Phe Gly Ala Tyr Met Ser Lys Ala His Gly Val Asp
65                  70                  75                  80

Pro Asn Ile Arg Thr Gly Val Arg Thr Ile Thr Thr Gly Ser Pro Ile
            85                  90                  95

Thr Tyr Ser Thr Tyr Gly Lys Phe Leu Ala Asp Gly Gly Cys Ser Gly
            100                 105                 110

Gly Ala Tyr Asp Ile Ile Ile Cys Asp Glu Cys His Ser Thr Asp Ala
            115                 120                 125

Thr Ser Ile Leu Gly Ile Gly Thr Val Leu Asp Gln Ala Glu Thr Ala
        130                 135                 140

Gly Ala Arg Leu Val Val Leu Ala Thr Ala Thr Pro Pro Gly Ser Val
145                 150                 155                 160

Thr Val Pro His Pro Asn Ile Glu Glu Val Ala Leu Ser Thr Thr Gly
            165                 170                 175

Glu Ile Pro Phe Tyr Gly Lys Ala Ile Pro Leu Glu Ala Ile Lys Gly
            180                 185                 190

Gly Arg His Leu Ile Phe Cys His Ser Lys Lys Lys Cys Asp Glu Leu
            195                 200                 205

Ala Thr Lys Leu Val Ala Leu Gly Ile Asn Ala Val Ala Tyr Tyr Arg
        210                 215                 220

Gly Leu Asp Val Ser Val Ile Pro Ser Ser Gly Asp Val Val Val Val
225                 230                 235                 240
```

```
Ala Thr Asp Ala Leu Met Thr Gly Phe Thr Gly Asp Phe Asp Ser Val
                245             250             255

Ile Asp Cys Asn Thr Cys Val Thr Gln Thr Val Asp Phe Ser Leu Asp
            260             265             270

Pro Thr Phe Thr Ile Glu Thr Thr Thr Leu Pro Gln Asp Ala Val Ser
        275             280             285

Arg Thr Gln Arg Arg Gly Arg Thr Gly Arg Gly Lys Pro Gly Ile Tyr
    290             295             300

Arg Phe Val Ala Pro Gly Glu Arg Pro Ser Gly Met Phe Asp Ser Ser
305             310             315                         320

Val Leu Cys Glu Cys Tyr Asp Ala Gly Cys Ala Trp Tyr Glu Leu Thr
                325             330             335

Pro Ala Glu Thr Thr Val Arg Leu Arg Ala Tyr Met Asn Thr Pro Gly
            340             345             350

Leu Pro Val Cys Gln Asp His Leu Glu Phe Trp Glu Gly Val Phe Thr
            355             360             365

Gly Leu Thr His Ile Asp Ala His Phe Leu Ser Gln Thr Lys Gln Ser
    370             375             380

Gly Glu Asn Phe Pro Tyr Leu Val Ala Tyr Gln Ala Thr Val Cys Ala
385             390             395             400

Arg Ala Gln Ala Pro Pro Ser Trp Asp Gln Met Trp Lys Cys Leu
            405             410             415

Ile Arg Leu Lys Pro Thr Leu His Gly Pro Thr Pro Leu Leu Tyr Arg
            420             425             430

Leu Gly Ala Val Gln Asn Glu Ile Thr Leu Thr His Pro Ile Thr Lys
            435             440             445

Tyr Ile Met Thr Cys Met Ser Ala Asp Leu Glu Val Val Thr
450             455             460
```

REAGENTS FOR HCV ANTIGEN-ANTIBODY COMBINATION ASSAYS

FIELD OF THE INVENTION

The present invention generally relates to immunoassays for detection and diagnosis of HCV infection. In particular, the present invention relates to combination immunoassays, reagents and kits based on use of a non-ionic detergent for simultaneous detection of HCV antigens and anti-HCV antibodies in a sample.

BACKGROUND OF THE INVENTION

The hepatitis C virus (HCV), a single-stranded RNA virus, is the etiological agent of blood-borne non-A, non-B hepatitis. Chronic active infection with HCV often progresses to liver cirrhosis and hepatocellular carcinoma. Epidemiological studies indicate that HCV infects more than 170 million people worldwide with a high incidence of chronic disease ultimately progressing (more than 50% of cases) to death. However, since it is mainly a blood-borne disease, it is possible to identify the pathogen in blood samples and to eliminate the transmission of disease through blood transfusion. After exposure to the HCV pathogen, there is initially no evidence of viral presence, i.e. no detectable viral RNA or serology markers. This is referred to as the "window period" (WP). Generally, after 10 days following exposure to HCV, viral RNA can be detected while anti-HCV antibodies become detectable approximately 70 days later (Busch M P and Dodd R Y, *Transfusion* 40(10): 1157-1160, 2000). To prevent spread of HCV infection, it is extremely important to take this observable fact into consideration and to establish a reliable blood-screening test, which would narrow the detection window. Since the commercialization of the nucleic acid amplification testing (NAT) which detects HCV RNA, the post-transfusion HVC infection rate has been dramatically reduced. Other methods are based on serological screening of the blood for detecting the presence of HCV core antigen (Ortho HCV Core Antigen ELISA, Ortho-Clinical Diagnostics, Inc., Raritan, N.J.) or antibodies against HCV polypeptides (Ortho HCV 3.0 ELISA, Ortho-Clinical Diagnostics, Inc., Raritan, N.J.) in patient serum or plasma.

According to a survey conducted by Seme et al. (*J. Clin. Virol.* 32(2): 92-101, 2005), the first generation HCV core antigen assay detects HCV infection with comparable sensitivity and detection limits to the nucleic acid techniques (NAT). These assays detect HCV infection between 40 to 50 days earlier than the current third generation HCV antibody screening assays. Although the first generation HCV core antigen assay, designed for blood screening, has significantly reduced the window period, it only detects core antigen at pre-seroconversion or early post-seroconversion phase. Furthermore, the first generation HCV core antigen assay is unable to detect core antigen when the antigen forms immune-complexes with anti-core antibodies in the late seroconversion phase. Clearly, it is desirable to have a combined serology assay that can detect HCV core antigen in the pre-seroconversion phase as well as anti-HCV antibodies in the seroconversion phase, thus narrowing the WP significantly. This combined serology test can especially be a valuable method of blood screening in settings where the NAT test can not be carried out due to lack of equipment or competency.

Such an HCV antigen and antibody combined assay will be a significant improvement over the current third generation serology blood screening method (Ortho HCV 3.0 ELISA, Ortho-Clinical Diagnostics, Inc., Raritan, N.J.) with regards to narrowing the WP. However, one of the challenges to the successful antigen antibody combined assay is to select an appropriate detergent to disrupt HCV virions and release antigen without interfering with the capture of anti-HCV antibodies by recombinant HCV antigens.

SUMMARY OF THE INVENTION

The present invention is directed to combination immunoassays, reagents and kits for simultaneous detection of HCV antigens and anti-HCV antibodies in a sample.

The uniqueness of the combination immunoassays of the present invention resides principally in the use of a non-ionic detergent that effectively exposes or releases the HCV core antigen from virions in a sample without any pre-processing of the sample, yet does not interfere with the capture of anti-HCV antibodies by recombinant HCV antigens, thereby permitting simultaneous measurement of the HCV core antigen and anti-HCV antibodies.

Non-ionic detergents suitable for use in the combination assays of the present invention are members of the N-alkyl-N,N-dimethyl-amine oxide family. In a preferred embodiment, the combination assay employs Lauryldimethylamine N-oxide (LDAO). In other embodiments, a derivative or functional or chemical equivalent of LDAO is employed.

Accordingly, the present invention provides combination immunoassays in various formats, related reagents and kits for simultaneous detection of HCV antigens and anti-HCV antibodies in a sample.

DETAILED DESCRIPTION OF THE INVENTION

The present invention is directed to HCV antigen-antibody combination immunoassays, and related methods, reagents and kits.

HCV antigen-antibody combination immunoassays or "combo" assays refer to immunoassays that simultaneously detect both HCV antigens and anti-HCV antibodies in a sample in a single assay. The antigen/antibody combination assay methods rely on the identification and use of antigenic and immunogenic HCV antibodies and antigens that are present during the early stages of HCV seroconversion, thereby increasing detection accuracy and reducing the incidence of false results during the window period.

The present invention is predicated, at least in part, on the identification of nonionic detergents that are suitable and effective for use in a combination immunoassay for sensitively and accurately detecting early HCV infection. Such detergents effectively disrupt HCV viral particles in a test sample and as a result, the released core antigen is effectively captured and detected by monoclonal antibody probes. In the meantime, the detergents do not impact negatively the antibody detection either by leaching the recombinant antigens coated on the solid-phase or by interfering with the capturing of anti-HCV antibodies during the combination assay. Therefore, the combination assays provided by the present invention permit simultaneous detection of both HCV antigens (including the core antigen) and anti-HCV antibodies in a sample in a single assay. Compared to the existing assays, including assays directed to detecting either HCV antigens or anti-HCV antibodies separately, the combination assays of the present invention circumvent the need to run two separate assays and provide improved sensitivity and specificity for HCV detection.

In accordance with the present invention, nonionic detergents suitable for use in a combination immunoassay include members of the N-alkyl-N-alkyl'-N-methyl-amine oxide family, which are also known as zwitter-ionic or zwitterionic detergents. The alkyl groups generally contain not more than 15 carbon atoms each.

In one embodiment, the detergent is an N-alkyl-N-alkyl'-N-methyl-amine oxide wherein the alkyl group is a mono-chain or branched alkyl group containing 9 to 13 carbon atoms, and the other alkyl group ("the alkyl" group) is a mono-chain or branched alkyl group containing 1 to 13 carbon atoms. In another embodiment, one or both the alkyl groups of N-alkyl-N-alkyl'-N-methyl-amine oxide are substituted alkyl groups.

In a preferred embodiment, the detergent is N-alkyl-N,N-dimethyl-amine oxide characterized by the formula:

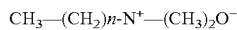

$$CH_3-(CH_2)_n-N^+-(CH_3)_2O^-$$

wherein the length of the alkyl chain is defined by the number n, which can be in the range of 9 to 13, or preferably 10 to 12, more preferably n is 11. The number "n" is at least 9; preferably at least 10; more preferably at least 11.

In an especially preferred embodiment of the present invention, the nonionic detergent employed in an HCV combination immunoassay is Lauryldimethylamine N-oxide (LDAO), having the formula of $CH_3-(CH_2)_{11}-N^+-(CH_3)_2O^-$, which is graphically depicted as:

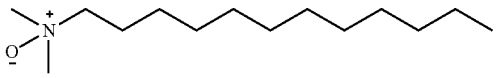 [SMILES: CCCCCCCCCCCC[N+](C)(C)[O-]]

A non-ionic detergent can be provided to a combination assay in any appropriate manner. For example, the detergent can be added to a test sample before the sample is placed in contact with detecting reagents such as capture antigens and antibodies. Alternatively, the detergent can be mixed with a test sample simultaneously with the addition of other reagents for detection. In a preferred embodiment, the detergent is provided in a solution (or "diluent"), which is used to dilute or suspend a biological test sample prior to contacting the sample with capture antigens and antibodies. Regardless of how a non-ionic detergent is provided to the assay, the concentration of the detergent in the solution mixture when the contact with the test sample occurs should be in the range of 0.1%-2% (w/v), preferably at least 0.3% (w/v) but not more than 1% (w/v), more preferably in about 0.5% (w/v).

Biological samples that can be tested for HCV using the combination assays of the present invention include any sample suspected to contain HCV virions, antigens or antibodies. The sample can be a biological fluid or tissue, including body fluids, such as whole blood, dried whole blood, serum, plasma, or other blood components including red blood cells, white blood cells and platelets; urine, saliva, cerebrospinal fluid, liver tissue, among others. The samples can be treated in any appropriate manner prior to being used in the assay.

In accordance with the present invention, the anti-HCV antibody detection part of the combination assay generally employs at least one (i.e., one or more) capture antigen that binds, therefore "captures" anti-HCV antibodies in the sample. The capture antigens are generally antigenic peptides (containing one or more epitopes) derived from an HCV protein encoded by the HCV genome. The sequence of the entire HCV genome and the encoded HCV polyprotein sequence are documented in GenBank (accession #M62321 and #AAA45676, respectively) and available to those skilled in the art.

It should be noted that the term "HCV protein" as used herein includes both a native, full-length protein encoded by the HCV genome (e.g., a structural or non-structural protein, or a precursor of a structural or non-structural protein), and an artificial fusion polypeptide of two native HCV proteins or fragments thereof (e.g., a fusion of NS3 and partial NS4, also referred herein as "NS3/NS4").

The term "HCV antigen" or "HCV antigens", as used herein in reference to antigens present in a sample from an HCV-infected individual, can be full-length HCV proteins or antigenic fragments thereof.

Generally speaking, a peptide fragment of an HCV protein is antigenic and capable of binding to and capturing the respective antibodies when the fragment is at least 6 or 7 amino acids in length, preferably, at least 8, or at least 9, or at least 10 amino acids; more preferably, at least 12, 15 or 20 amino acids. Capture HCV antigens can contain more than one epitope. The term "epitope" is well understood in the art and refers to a molecular region or structural determinant on the surface of an antigen capable of binding to an antibody and eliciting an immune response. Capture antigens can be made recombinantly, or by conventional chemical synthesis.

In certain embodiments, the capture antigen is an antigenic fragment of an HCV protein selected from core antigen, E1, E2, NS2, NS3, NS4, or NS5. In a preferred embodiment, the capture antigen is derived from core antigen, or an NS3/NS4 fusion protein as illustrated in the examples below. In another embodiment, two or more peptides are used as capture antigens, which can be derived from the same or different HCV proteins.

A capture antigen can be coated on a solid phase prior to performing the assay. Alternatively, the capture antigen is conjugated with an appropriate reagent, e.g., biotin, which can mediate attachment to a solid phase after the capture antigen has formed a complex with (i.e., has captured) anti-HCV antibodies in a liquid phase, e.g., in a cocktail ELISA format.

Examples of solid phases suitable for use in the immunoassays of the present invention include both porous and non-porous materials, such as, for example, latex particles, magnetic particles, beads, membranes, and microtiter wells. The choice of solid phase material can be determined based upon desired assay format.

When a capture antigen is contacted with a test sample, if anti-HCV antibodies are present in the sample, such antibodies bind to the capture antigen. The antibodies captured by the capture antigen, i.e., the captured antibodies, can be detected using a number of approaches.

One approach utilizes a second antibody, which recognizes and binds the captured HCV antibodies. The second antibody, e.g., anti-human IgG, is conjugated to a signal-generating means. When the second antibody binds to a captured (first) antibody, the signal-generating means generates a measurable signal, which indicates the presence of the first antibody in the test sample.

Another approach utilizes a second antigen, which can be conjugated to a signal-generating means, and is also referred to as a "detection antigen". Like capture antigens, a detection antigen can also contain more than one epitope, as long as one common epitope is present on both the capture antigen and the detection antigen. Additionally, one or more detection antigens can be used. When a detection antigen binds to a captured antibody thereby forming a capture antigen-antibody-detection antigen sandwich, the signal-generating means in the detection antigen can generate a measurable signal, which indicates the presence of the antibody in the test sample. This "Ag sandwich" approach is premised on the ability of an anti-HCV antibody to simultaneously bind two identical epitopes in two separate antigen molecules. This Ag-sandwich approach permits highly specific detection of the anti-HCV antibodies; and because of this high specificity, this approach allows for the use of a larger volume of a test sample, which in turn permits a more sensitive detection of HCV antigens present in the sample.

This signal-generating means is either itself detectable or may be reacted with one or more compounds to generate a detectable signal. Examples of signal-generating means include chromogens, radioisotopes, chemiluminescent compounds, enzymes (e.g., alkaline phosphatase, acid phosphatase, horseradish peroxidase, beta-galactosidase and ribonuclease), or one partner of a binding pair (such as biotin or strepavidin). Where an enzyme is used as a signal-generating means (e.g., alkaline phosphatase or horseradish peroxidase), addition of a chromo-, fluro-, or lumo-genic substrate results in generation of a detectable signal.

In accordance with the present invention, the HCV antigen detection part of the combination assay is generally achieved using one or more pairs of a capture antibody and a conjugate antibody in an antibody sandwich format.

The conjugate antibody is attached with any one of the signal-generating means described hereinabove. The capture antibody can be coated on a solid phase, i.e., the same solid phase as the capture antigen(s) described above, prior to performing the assay. Alternatively, the capture antibody is conjugated with an appropriate reagent, e.g., biotin, which can mediate attachment to a solid phase after the capture antibody has formed a complex with (i.e., has captured) an HCV antigen in a liquid phase which is either already or subsequently bound with a conjugate antibody. In either approach, once a capture antibody-antigen-conjugate antibody sandwich is formed and captured onto a solid phase, the signal-generating means can generate a measurable signal, which indicates the presence of the antigen in the test sample.

Within each pair, there can be one or more capture antibodies each recognizing different epitopes, and one or more conjugate antibodies each recognizing different epitopes. In order to permit simultaneous binding of the capture and conjugate antibodies to the same antigen molecule and formation of a sandwich complex, the capture antibody or antibodies should recognize different epitopes from those recognized by the conjugate antibody or antibodies in the same pair, yet the epitopes recognized by the capture and conjugate antibodies, respectively, should be within the same HCV antigen in order to form an antibody-antigen-antibody sandwich. For example, the capture and conjugate antibodies can be directed to epitopes in any HCV protein, structural or non-structural HCV polypeptide, encoded by the HCV genome. Preferably, the antibodies are directed to epitopes within an HCV protein selected from the core antigen, E1, E2, NS2, NS3, NS4, or NS5. In an especially preferred embodiment, the capture and conjugate antibodies in one pair are directed to, i.e., specifically bind to, epitopes within the HCV core antigen. In another embodiment, two or more pairs of capture and conjugate antibodies are used, and at least one of the pairs includes a capture and a conjugate antibody directed to epitopes within the HCV core antigen.

The capture and conjugate antibodies can be monoclonal antibodies or polyclonal antibodies or combinations thereof. Preferably, monoclonal antibodies are employed.

To perform a combination assay in accordance with the present invention, one is provided with a capture antigen and either a conjugate antibody or a detection antigen for detecting anti-HCV antibodies; a capture antibody and an HCV-specific antibody conjugate for detecting HCV antigens; and an appropriate non-ionic detergent. A test sample is contacted with the detergent, the capture and conjugate reagents, sequentially or simultaneously, and the signal generated from the conjugate reagents can be correlated with a diagnosis of HCV infection.

In a specific embodiment, one is provided with a capture antigen, a detection antigen; a capture antibody and a conjugate antibody; and an appropriate non-ionic detergent. In a preferred embodiment, the capture antigen and the capture antibody are both coated on (covalently or non-covalently attached to) a solid phase. A test sample is brought into contact with the capture reagents attached to the solid phase in the presence of the detergent. Simultaneously or preferably subsequently, the conjugate reagents (i.e., detection antigen and conjugate antibody) are added to the reaction mixture. The signal generated as a result of the binding of the conjugate reagents also to the solid phase can be correlated with a diagnosis of HCV infection.

It should be noted that the capture and conjugate reagents should be chosen to avoid cross-reactivity and false-positive results. For example, the HCV antigens employed for detecting anti-HCV antibodies are derived from an HCV polypeptide different from the polypeptide against which the capture and conjugate antibodies are directed. Alternatively, when the antigens employed for antibody detection are derived from the same HCV protein (e.g., the core antigen) as the protein against which the antibody reagents are raised, the antigens used for antibody detection should present epitopes that are not recognized by the antibody reagents used for antigen detection. Essentially, the epitopes to which antibodies bind in the antigen detection part of the assay should not be present in the antigens used for HCV antibody detection.

The present invention also provides kits containing the various reagents described above for performing a combination assay in order to simultaneously detect HCV antigens and anti-HCV antibodies in support of a diagnosis of HCV infection.

EXAMPLES

The following examples describe in detail the advantages and importance of the invention by examining the detergent Lauryldimethylamine N-oxide (LDAO) and its efficiency in achieving release of the HCV core antigen in an antigen assay and its compatibility with an HCV antibody assay. The use of detergent Lauryldimethylamine N-oxide (LDAO) in simultaneous measurement of HCV core antigen and HCV antibodies is also described.

It is to be understood that the examples presented hereinbelow are for illustration and are not intended to limit the scope of the present invention.

General Reagents for HCV Core Antigen and Anti-HCV Antibody Detection
Ortho HCV Core Antigen ELISA Test System Ortho HCV Core Antigen ELISA (Ortho-Clinical Diagnostics, Inc., Raritan, N.J.) was used for the detection of hepatitis C nucleocapsid core antigen (HCV core antigen) in human serum or plasma. The monoclonal antibodies coated onto the microwell solid phase were used to capture the antigen and the secondary monoclonal antibodies conjugated to HRP were used to detect the captured antigen. A detergent-containing specimen diluent was used to expose the HCV core antigen for capture and detection without a pretreatment step.

Ortho HCV 3.0 ELISA Test System

Ortho HCV 3.0 ELISA (Ortho-Clinical Diagnostics, Inc., Raritan, N.J.) was for the detection of antibody to hepatitis C virus (anti-HCV) in human serum or plasma. The recombinant HCV antigens c22 (amino acid 2-120, core region), c200 (amino acid 1192-1931, NS3/NS4 region) and NS5 (amino acid 2054-2995) coated on to the microwell solid phase were used to capture the anti-HCV antibodies. Murine monoclonal anti-human IgG antibody conjugated to HRP was used to detect the captured human anti-HCV. This format utilizes detergent Tween 20 in the specimen diluent.

Chiron RIBA HCV 3.0 SIA

Chiron RIBA HCV 3.0 SIA (Novartis Vaccines & Diagnostics, Emeryville, Calif.) is a strip immunoblot assay used for the detection of antibody to hepatitis C virus (anti-HCV) in human serum or plasma. The HCV antigens or peptides c22p (amino acid 10-53, core region), c33c (amino acid 1192-1457, NS3 region), 5-1-1 and c100 peptides (amino acid 1694-1735 and 1920-1935 respectively, NS4 region) and NS5 (amino acid 2054-2995) were immobilized as individual bands onto test strips to capture the anti-HCV antibodies. Murine monoclonal anti-human IgG antibody conjugated to HRP then detected the captured human anti-HCV. The assay provides additional information on antibody specific reactivity to individual antigen of an Ortho HCV 3.0 ELISA reactive specimen.

Antigens

Two peptide derivatives were synthesized to cover the HCV core protein sequence from amino acid 10 to amino acid 45. For HCC5N, the sequence is set forth in SEQ ID NO:1 (the N-terminus has a free amino group, as opposed to an amino group blocked by acetylation). HCC5N has two residues at the C-terminus, NorLeucine and Cys, which do not belong to the HCV core protein. For HCC5-b, the sequence is set forth in SEQ ID NO:2 (the N-terminus has a free amino group). HCC5-b has two residues at the C-terminus, Gly and Lys(Biotin), which do not belong to the HCV core protein. HCC5N was further conjugated to SMCC activated BSA through the C-terminal Cys of HCC5N under reducing conditions.

Recombinant HCV NS3 helicase (rNS3(h)), covering residues P1208 to T1657, was cloned and expressed in *E. coli* as described previously (Jin, Arch Biochem Biophys. 323(1): 47-53, 1995). A 6×His tag was fused to the N-terminus of the rNS3(h) to purify protein (resulting in SEQ ID NO:3, representing a fusion protein of the 6×His tag and rNS3(h)). A biotin conjugated rNS3(h) was made using EZ-Link Sulfo-NHS-LC-Biotin (Pierce, Cat#21335). The conjugated protein was determined to have 3 biotins per rNS3(h) molecule.

Monoclonal Anti-HCV Core Antibodies

Four monoclonal antibodies were used in the study. The production and epitope recognition sites of monoclonal antibody C11-3, C11-7 and C11-14 have been described in European Patent Publication EP 0 967 484 A1. None of the epitope recognition sites of these monoclonal antibodies fall within amino acids 10-45 of HCV. The monoclonal anti-HCV antibody 12F11 was raised against recombinant c22. The recognition site of 12F11 is around amino acids 58-72 of HCV (core antigen). The antibodies C11-14 and 12F11 were conjugated to horseradish peroxidase (HRP) using standard procedures.

HCV Specimens (1) Anti-c22 and Anti-c33c Depleted Anti-HCV Specimens

Specimens WHO Hu-a-c33c, 41530822, 41530832 and 41530883 were originally tested anti-HCV strong reactive by Ortho HCV 3.0 ELISA and non-reactive by Ortho HCV Core Antigen ELISA. The anti-c22 portion (anti-HCV core) of the antibodies was depleted by passing the specimen through an affinity column in which chromatography resins were conjugated with recombinant HCV core antigen c22, the same antigen as one of the coating antigens used in the Ortho HCV 3.0 ELISA.

Specimen WHO Hu-a-c22, I-20 and 360650 were originally tested anti-HCV strong reactive by Ortho HCV 3.0 ELISA and non-reactive by Ortho HCV Core Antigen ELISA. The anti-c33c portion (anti-partial NS3) of the antibodies was depleted by passing the specimen through an affinity column in which chromatography resins were conjugated with recombinant HCV core antigen c33, the same antigen (c33c) immobilized in the Chiron RIBA 3.0 SIA and a shorter version of one of the coating antigens (c200) used in the Ortho HCV 3.0 ELISA.

(2) HCV Core Antigen Reactive Specimen

HCV core antigen reactive sample Lot 16 was a plasma pool, made of specimens that were tested non-reactive of anti-HCV by Ortho HCV 3.0 ELISA, reactive of HCV RNA by PCR, and reactive of HCV core antigen by Ortho HCV Core Antigen ELISA. HCV core antigen sample 9160834 is a plasma specimen from Boston Biomedica Inc. (BBI). The specimen was tested non-reactive to anti-HCV by Ortho HCV 3.0 ELISA, reactive to HCV RNA at about 36,379,940 IU/mL or 189,175,500 copies/mL by Versant bDNA (Bayer), and reactive to Ortho HCV Core Antigen ELISA.

(3) HCV Seroconversion Panels

HCV Seroconversion Panels tested in the present studies were all commercially available, purchased from SeraCare Life Sciences, Inc. USA (BBI Diagnostics) and ZeptoMetrix Corporation, USA (former Impath/BioClinical Partners, Inc.). A HCV Seroconversion Panel was composed of serial bleeds of human blood specimens taken from an individual who was infected with HCV. Specimens covered a period from anti-HCV non-reactive to reactive.

Example 1: Anti-HCV Antibody Detection (an Indirect Assay Format)

The assays were performed using reagents from an Ortho HCV 3.0 ELISA kit. 150 µL specimen diluents composed of a phosphate based buffer containing detergent Tween-20, BSA, casein, yeast extracts and other proteins, plus 50 µL specimen were added to each well. The plates were incubated at 37° C. for 60 minutes, and were then washed 5 times with a PBS/Tween20-containing wash buffer. Afterwards 200 µL HRP conjugated murine monoclonal anti-human IgG antibody was added to each well. The plates were incubated at 37° C. for 60 minutes and subsequently washed 6 times. 200 µL OPD/substrate (one OPD tablet (Sigma, Cat# P-8287) in 6 mL of ELISA substrate buffer) was added to each well and the plates were incubated in the dark at room temperature for 30 minutes. A 4N $H_2SO_4$ stop solution was added at 50 µL/well. ODs were recorded at 493 nm using a plate spectrophotometry reader. Assay cut-off setting was adapted from HCV 3.0 ELISA that is OD of average negatives plus 0.6. The assay exceptions were:

(1) In "ELISA-1", specimen diluent was from the kit, containing detergent Tween 20; while in "ELISA-2", the detergent was replaced with N-Lauryl sarcosine (NLS), and in "ELISA-3", the detergent was replaced with Lauryldimethylamine N-oxide (LDAO).

(2) In "ELISA-1", the HRP-conjugated murine monoclonal anti-human IgG antibody, provided in the kit, was diluted at 1:3 prior to use; and in "ELISA-2" and "ELISA-3", the conjugated antibody provided in the kit was diluted at 1:2 prior to use.

As shown in Table 1, for both anti-c22 and anti-c33c depleted specimens, Tween20 (commonly used in anti-HCV antibody detection) and LDAO each provided better assay sensitivity, as reflected by the signal vs. cut-off ratios ("S/C"), than NLS (typically used in HCV antigen detection).

Example 2: Anti-HCV Antibody Detection (Ag Sandwich Assay Format)

In the Ag sandwich assay format, antigens labeled with biotin were used as conjugate. The biotin-antigen conjugates bound to human anti-HCV antibodies that were captured on solid phase to form an Ag-Ab-Ag sandwich. The sandwiched complexes were then detected by HRP conjugated streptavidin in a subsequent incubation.

COSTA™ high-binding microtiter plates were coated with 200 µL/well of premixed monoclonal antibodies C11-3 and C11-7 at 2.2 µg/mL of each and HCC5N-BSA at 0.1 µg/mL in 20 mM phosphate buffer (pH 7.0). The plates were incubated at 25° C. overnight. The coating solutions were aspirated and 200 µl/well of rNS3(h) at 2 µg/mL in PB (pH7.0) was added. Plates were incubated at 25° C. overnight. The plates were then washed one time with PBS/Tween wash buffer, followed by addition of 300 µL/well PBS/BSA blocking solution (1% bovine serum albumin and 30% sucrose in PBS) for 1 hour at 25° C. The plates were aspirated and dried overnight at 25° C. with 10% humidity and pouched with desiccant.

Specimen diluent composition was the same as used in Example 1, except for containing detergent Tween 20 in "ELISA-4", detergent N-Lauryl sarcosine (NLS) in "ELISA-5", and detergent Lauryldimethylamine N-oxide (LDAO) in "ELISA-6". 100 µL specimen diluent and 100 µL specimen were added to each well. The specimen incubation was at 37° C. for 1 hour with shake. The plates were then washed 5 times with PBS/Tween20. 200 µL biotin-rNS3(h) (or "rNS3(h)-b") was added at 60 ng/mL or biotin-HCC5 (HCC5-b) was added at 5 ng/mL to each well. Biotin-antigen was diluted in conjugate diluent CD-1 (Casein Blocker in PBS, Pierce Cat#37528, supplemented with Tween 20 to 0.05% and EDTA to 2 mM). The biotin-antigen incubation was kept at 37° C. for 60 minutes with shake. The plates were washed 5 times and HRP-Streptavidin (Jackson ImmunoResearch, Cat#016-030-084) 1:8,000 diluted in CD-1 was added at 200 µL/well. The HRP-Streptavidin incubation was kept at room temperature for 30 minutes. The plates were then washed 6 times, after which 200 µL OPD/substrate was added to each well. The plates were incubated in the dark at room temperature for 30 minutes, and an aliquot of 50 µL 4N $H_2SO_4$ stop solution was added to each well. ODs were recorded at 493 nm using a plate spectrophotometry reader. Assay cut-off was determined as OD of negative average plus 0.300. Assay results are shown in Table 2. The results show that with the anti-c33c depleted specimen, Tween20 and LDAO each provided better assay sensitivity than NLS.

The results also demonstrate that the antigen sandwich format (Ag-Ab-Ag) is better than the indirect format (Ag-Ab-$2^{nd}$ Ab).

Example 3: HCV Core Antigen Detection

The HCV core antigen detection shown in Example 3 was a monoclonal antibody-HCV core antigen-monoclonal antibody sandwich ELISA. The exposed HCV core antigen in specimen was captured by two monoclonal anti-HCV core antibodies coated on plates and detected by another two HRP labeled monoclonal anti-HCV antibodies.

Except specimen diluent, ELISA reagents used in Example 3 were basically from the Ortho HCV Core Antigen ELISA kit. "ELISA-7" used the original Kit specimen diluent that contained 1.0% detergent N-Lauroylsarcosine (NLS). However, "ELISA-8" used specimen diluent containing 1.0% detergent Tween 20 and "ELISA-9" used specimen diluent containing 1.0% detergent Lauryldimethylamine N-oxide (LDAO).

ELISA was performed following HCV Core Antigen ELISA's protocol. 100 uL specimen diluent and 100 µL specimen were added to each well. The specimen incubation was performed at 37° C. for 90 minutes with shake. The plate was washed 5 times with PBS/Tween20 and conjugate antibodies were added at 200 µl to each well. The conjugate incubation was performed at 37° C. for 30 minutes. The plate was washed 6 times and 200 µL OPD/substrate was added to each well. The plate was then incubated in the dark at room temperature for 30 minutes. A 4N $H_2SO_4$ stop solution was then added at 50 µL/well. ODs were recorded at 493 nm using a plate spectrophotometer reader. Assay cut-off setting was similar to HCV Core Antigen ELISA, i.e., the OD of negative average plus 0.300.

Assay results are shown in Table 3. For specimens, NLS and LDAO each provided better assay sensitivity than Tween20.

Example 4: HCV Core Antigen/Anti-HCV Combination Assay

HCV core antigen/anti-HCV antibody combination ELISA was performed on the same plates as used in Example 2. Plates were coated with monoclonal anti-HCV antibody C11-3 and C11-7, HCC5-BSA and rNS3(h). Specimen diluent was composed of 20 mM phosphate buffer (pH 7.3), 0.5M Sodium Chloride, 1 mM EDTA, 1% detergent LDAO, 1% BSA, 0.03% Yeast extracts and 0.01% denatured Superoxidase Dismutase (SOD), 200 µg/mL mouse immunoglobulin G (IgG) and 0.1% 2-Chloroacetamide. The antibody/antigen conjugate was composed of HRP labeled anti-HCV monoclonal antibody C11-14 at 4 µg/mL and HRP labeled monoclonal antibody 12F11 at 4 µg/mL, HCC5-biotin at 5 ng/mL and rNS3(h)-biotin at 60 ng/mL in a buffer of 10 mM phosphate buffer (pH 7.3), 142 mM sodium chloride, 3 mM potassium chloride, 0.1% detergent Tween 20, 1.5% BSA, 20% heat inactivated Newborn Calf Serum, 0.03% potassium ferricyanide, 100 ug/mL mouse immunoglobulin G (monoclonal) and 0.1% 2-Chloroacetamide. The HRP labeled Streptavidin conjugate was composed of HRP-Streptavidin (Jackson ImmunoResearch, Cat#016-030-084) 1:8,000 diluted in CD-1 (Casein Blocker in PBS, Pierce Cat#37528, added Tween 20 to 0.05% and EDTA to 2 mM).

Assay protocol was the same as described in Example 2. 100 uL specimen diluent and 100 uL specimen were added to each well. Plates were then incubated at 37° C. for 1 hour with shake, followed by washing 5 times with PBS/

Tween20. 200 μL antibody/antigen conjugate mixture was then added to each well. The antibody/antigen conjugate incubation was performed at 37° C. for 60 minutes with shake. The plates were then washed 5 times, 200 μL/well HRP-Streptavidin was subsequently added, and the plates were incubated at room temperature for 30 minutes. Afterwards the plates were washed 6 times, 200 μL OPD/substrate was added to each well, and the plates were incubated in the dark at room temperature for 30 minutes. 50 μL/well 4N $H_2SO_4$ stop solution was added, and ODs were recorded at 493 nm using a plate spectrophotometry reader. Assay cut-off was set at 0.300.

Assay results of HCV antigen/antibody combination ELISA on BBI HCV seroconversion panels are shown in Table 4. Assay results of HCV antigen/antibody combination ELISA on ZeptoMetrix HCV seroconversion panels are shown in Table 5. It can be seen that at an early infection stage, detection was negative in the antibody detection assay, whereas detection was positive using the HCV RNA assay, the HCV antigen assay, or the HCV antigen-antibody combination assay. See, for example, Table 4, with "PHV907", days 4, 7 and 13 from first bleed. On the other hand, at a later stage of infection (e.g., day 164 with "PHV907"), when detection of antigen became negative and the quantity of HCV RNA was reduced, anti-HCV antibodies were strongly detected in the antibody detection assay, and the S/C ratio was also well above 1 in the antigen-antibody combination assay. These results demonstrate that the HCV antigen-antibody combination assay provided a wider window of detection than an assay based on detection of either HCV antigen or anti-HCV antibody alone.

TABLE 1

Detergent comparison in the indirect format anti-HCV assay.

| | | | | ELISA assays and format | | | | |
|---|---|---|---|---|---|---|---|---|
| | | | | ELISA-1 Indirect | | ELISA-2 Indirect | | ELISA-3 Indirect |
| | | | | Detergent in specimen diluent | | | | |
| | | | | Tween20 (0.25%) | | NLS (0.67%) | | LDAO (0.67%) |
| | | | | Kit's conjugate dilution | | | | |
| | | | | 1:3 | | 1:2 | | 1:2 |
| | | | | OD | S/C | OD | S/C | OD | S/C |
| Negative plasma | | | | 0.001 | | 0.001 | | 0.002 | |
| | | | | 0.002 | | 0.002 | | 0.001 | |
| | | | | 0.002 | | 0.001 | | 0.001 | |
| | | | RIBA3.0 | | | | | | |
| HCV Specimens | | Dilution | c33c | c22p | | | | | |
| anti-c22 depleted specimens | WHO | 1:25 | 2+ | − | 2.122 | 3.5 | 0.745 | 1.2 | 1.773 | 2.9 |
| | Hu-a-c33c | 1:50 | 2+ | − | 1.179 | 2.0 | 0.414 | 0.7 | 0.985 | 1.6 |
| | | 1:100 | 1+ | − | 0.911 | 1.5 | 0.297 | 0.5 | 0.707 | 1.2 |
| | | 1:200 | + | − | 0.608 | 1.0 | 0.230 | 0.4 | 0.547 | 0.9 |
| | 41530822 | 1:25 | +/− | − | 1.235 | 2.1 | 0.306 | 0.5 | 1.094 | 1.8 |
| | | 1:50 | +/− | − | 0.686 | 1.1 | 0.170 | 0.3 | 0.608 | 1.0 |
| | | 1:100 | +/− | − | 0.441 | 0.7 | 0.089 | 0.1 | 0.212 | 0.4 |
| | 41530832 | 1:100 | 2+ | − | 0.808 | 1.3 | 0.322 | 0.5 | 0.765 | 1.3 |
| | | 1:200 | + | − | 0.648 | 1.1 | 0.230 | 0.4 | 0.547 | 0.9 |
| | | 1:400 | +/− | − | 0.325 | 0.5 | 0.084 | 0.1 | 0.201 | 0.3 |
| | 41530883 | 1:200 | + | − | 0.985 | 1.6 | 0.203 | 0.3 | 0.590 | 1.0 |
| | | 1:400 | +/− | − | 0.547 | 0.9 | 0.113 | 0.2 | 0.268 | 0.4 |
| | | 1:800 | +/− | − | 0.276 | 0.5 | 0.053 | 0.1 | 0.127 | 0.2 |
| anti-c33c depleted specimens | WHO | 1:25 | − | 4+ | 1.346 | 2.2 | 1.146 | 1.9 | 1.678 | 2.8 |
| | Hu-a-c22 | 1:50 | − | 4+ | 1.165 | 1.9 | 0.895 | 1.5 | 1.439 | 2.4 |
| | | 1:100 | − | 2+ | 0.772 | 1.3 | 0.420 | 0.7 | 0.675 | 1.1 |
| | I-20 | 1:100 | − | 3+ | 0.896 | 1.5 | 0.538 | 0.9 | 0.865 | 1.4 |
| | | 1:200 | − | 2+ | 0.410 | 0.7 | 0.230 | 0.4 | 0.370 | 0.6 |
| | 360650 | 1:100 | − | 3+ | 0.637 | 1.1 | 0.380 | 0.6 | 0.611 | 1.0 |
| | | 1:200 | − | 2+ | 0.325 | 0.5 | 0.197 | 0.3 | 0.316 | 0.5 |
| | | 1:400 | − | + | 0.171 | 0.3 | 0.108 | 0.2 | 0.173 | 0.3 |
| | | cut-off | | | 0.602 | | 0.601 | | 0.601 | |

TABLE 2

Detergent comparison in the Ag sandwich format anti-HCV assay.

| | | | | ELISA assays and format | | | | | | |
|---|---|---|---|---|---|---|---|---|---|---|
| | | | | ELISA-4 Ag sandwich | | ELISA-5 Ag sandwich | | ELISA-6 Ag sandwich | | Ag-biotin conjugate |
| | | | | Detergent in specimen diluent | | | | | | |
| | | | | Tween20 (0.25%) | | NLS (1%) | | LDAO (1%) | | |
| | | | | OD | S/C | OD | S/C | OD | S/C | |
| Negative plasma | | | | 0.044 | | 0.012 | | 0.013 | | rNS3(h)-b |
| | | | | 0.013 | | 0.008 | | 0.010 | | at 60 ng/mL |
| | | | | 0.018 | | 0.020 | | 0.030 | | HCC5-b |
| | | | | 0.036 | | 0.017 | | 0.027 | | at 5 ng/mL |
| | | | RIBA3.0 | | | | | | | |
| HCV Specimens | | Dilution | c33c | c22p | | | | | | |
| anti-c22 depleted specimens | WHO Hu-a-c33c | 1:100 | 1+ | – | 2.997 | >9 | 2.997 | >9 | 2.997 | >9 | rNS3(h)-b at 60 ng/mL |
| | | 1:200 | +/– | – | 2.997 | >9 | 2.997 | >9 | 2.997 | >9 | |
| | | 1:400 | +/– | – | 1.567 | 4.8 | 1.922 | 6.4 | 1.446 | 4.8 | |
| | | 1:800 | – | – | 0.470 | 1.4 | 0.754 | 2.5 | 0.427 | 1.4 | |
| | 41530822 | 1:100 | +/– | – | 0.560 | 1.9 | 1.720 | 5.7 | 0.580 | 1.9 | |
| | | 1:200 | – | – | 0.284 | 0.9 | 0.724 | 2.4 | 0.236 | 0.8 | |
| | 41530832 | 1:200 | +/– | – | 2.997 | >9 | 2.997 | >9 | 2.997 | >9 | |
| | | 1:400 | +/– | – | 1.418 | 4.7 | 2.538 | 8.5 | 1.984 | 6.6 | |
| | | 1:800 | +/– | – | 0.232 | 0.8 | 0.720 | 2.4 | 0.360 | 1.2 | |
| | 41530883 | 1:200 | + | – | 2.800 | 9.3 | 2.997 | >9 | 2.997 | >9 | |
| | | 1:400 | +/– | – | 0.510 | 1.7 | 1.560 | 5.2 | 0.838 | 2.8 | |
| | | 1:800 | – | – | 0.168 | 0.6 | 0.612 | 2.0 | 0.294 | 1.0 | |
| | Cut-off | | | | 0.329 | | 0.310 | | 0.372 | | |
| anti-c33c depleted specimens | WHO Hu-a-c22 | 1:200 | – | 2+ | 2.119 | 6.5 | 0.174 | 0.5 | 2.997 | >9 | HCC5-b at 5 ng/mL |
| | | 1:400 | – | 1+ | 1.588 | 4.9 | 0.117 | 0.4 | 2.858 | 8.7 | |
| | | 1:800 | – | +/– | 1.122 | 3.4 | 0.066 | 0.2 | 1.909 | 5.8 | |
| | I-20 | 1:200 | – | 2+ | 0.637 | 1.9 | 0.087 | 0.3 | 1.127 | 3.4 | |
| | | 1:400 | – | 2+ | 0.343 | 1.0 | 0.050 | 0.2 | 0.610 | 1.9 | |
| | | 1:800 | – | +/– | 0.185 | 0.6 | 0.046 | 0.1 | 0.310 | 0.9 | |
| | 360650 | 1:200 | – | 2+ | 1.659 | 5.1 | 0.137 | 0.4 | 2.086 | 6.4 | |
| | | 1:400 | – | 2+ | 0.739 | 2.3 | 0.075 | 0.2 | 1.156 | 3.5 | |
| | | 1:800 | – | +/– | 0.337 | 1.0 | 0.056 | 0.2 | 0.592 | 1.8 | |
| | Cut-off | | | | 0.327 | | 0.379 | | 0.329 | | |

TABLE 3

Detergent comparison in HCV Core Ag assay.

| | | ELISA assays | | | | | |
|---|---|---|---|---|---|---|---|
| | | ELISA-7 | | ELISA-8 | | ELISA-9 | |
| | | | | Detergent in SD | | | |
| | | NLS (1.0%) | | Tween20 (1.0%) | | LDAO (1.0%) | |
| | | OD | S/C | OD | S/C | OD | S/C |
| Negative plasma | | 0.010 | | 0.014 | | 0.011 | |
| | | 0.010 | | 0.017 | | 0.008 | |
| | | 0.008 | | 0.013 | | 0.009 | |
| | Dilution | | | | | | |
| Lot 16, a pool of plasma specimens that were all characterized as anti-HCV (–), HCV RNA (+) and HCV core Ag (+) | neat | 0.722 | 15 | 0.300 | 5.5 | 1.852 | 38 |
| | 1:1.5 | 1.075 | 22 | 0.189 | 3.5 | 1.220 | 25 |
| | 1:2.0 | 1.115 | 23 | 0.149 | 2.7 | 0.948 | 19 |
| | 1:3.0 | 0.802 | 16 | 0.103 | 1.9 | 0.621 | 13 |
| | 1:4.0 | 0.602 | 12 | 0.074 | 1.3 | 0.431 | 8.8 |
| | 1:5.0 | 0.490 | 9.9 | 0.064 | 1.2 | 0.335 | 6.8 |
| | 1:6.0 | 0.379 | 7.7 | 0.051 | 0.9 | 0.279 | 5.7 |
| | 1:8.0 | 0.271 | 5.5 | 0.041 | 0.7 | 0.199 | 4.1 |
| | 1:10 | 0.214 | 4.3 | 0.040 | 0.7 | 0.148 | 3.0 |
| | 1:16 | 0.155 | 3.1 | 0.026 | 0.5 | 0.104 | 1.0 |

TABLE 3-continued

Detergent comparison in HCV Core Ag assay.

| | Dilution | X million IU/ml (copies/ml) | | | | | | |
|---|---|---|---|---|---|---|---|---|
| 9160834 @ | 1:5 | 7.28 (37.8) | 1.390 | 28 | 0.178 | 3.2 | 1.121 | 23 |
| $36.4 \times 10^6$ | 1:10 | 3.64 (18.9) | 0.734 | 15 | 0.086 | 1.6 | 0.527 | 11 |
| IU/ml or | 1:20 | 1.82 (9.46) | 0.364 | 7.4 | 0.047 | 0.9 | 0.251 | 5.1 |
| $189 \times 10^6$ | 1:30 | 1.21 (6.31) | 0.253 | 5.1 | 0.036 | 0.6 | 0.157 | 3.0 |
| copies/ml | 1:40 | 0.91 (4.73) | 0.181 | 3.7 | 0.028 | 0.5 | 0.116 | 2.4 |
| | cut-off | | | 0.049 | | 0.055 | | 0.049 |

TABLE 4

HCV antigen/antibody combination assay on BBI HCV seroconversion panels

| Seroconversion Panels | | Days from 1st | anti-HCV RIBA 3.0 | | HCV 3.0 | HCV RNA | | HCV Ag (HCV core) | HCV Ag/Ab combination assay | |
|---|---|---|---|---|---|---|---|---|---|---|
| ID | Bleed | bleed | c22p | c33c | S/C | testing kit | quantity | Pos or (Neg) | OD | S/C |
| | | | | | | From Panel Data Sheet | | | | |
| PHV907 | 1 | 0 | − | − | 0.0 | HCV RNA | $>5 \times 10^5$ | pos | 0.311 | 1.04 |
| genotype | 2 | 4 | − | − | 0.0 | Roche | $>5 \times 10^5$ | pos | 0.317 | 1.06 |
| 1b | 3 | 7 | − | − | 0.0 | Amplicor | $>5 \times 10^5$ | pos | 0.371 | 1.24 |
| | 4 | 13 | 1+ | − | 0.1 | PCR (BBI) | $>5 \times 10^5$ | pos | 0.437 | 1.46 |
| | 5 | 18 | 4+ | +/− | 0.4 | copies/ml | $>5 \times 10^5$ | pos | 0.877 | 2.92 |
| | 6 | 21 | 4+ | 1+ | 1.0 | | $>5 \times 10^5$ | pos | 2.442 | 8.14 |
| | 7 | 164 | 4+ | 4+ | 4.4 | | $4 \times 10^4$ | neg | >3 | >10 |
| PHV909 | s1 | 0 | − | − | 0.0 | | $1 \times 10^4$ | pos | 0.305 | 1.02 |
| genotype | 2 | 28 | 1+ | − | 1.3 | | $4 \times 10^4$ | pos | 0.701 | 2.34 |
| 3 | 3 | 30 | 2+ | − | 1.3 | | $2 \times 10^4$ | pos | 0.960 | 3.20 |
| PHV910 | 1 | 0 | − | − | 0.0 | | $>5 \times 10^5$ | pos | 0.599 | 2.00 |
| genotype | 2 | 4 | − | − | 0.0 | | $>5 \times 10^5$ | pos | 0.424 | 1.41 |
| 1b | 3 | 8 | 3+ | 1+ | 3.0 | | $>5 \times 10^5$ | pos | 1.497 | 4.99 |
| | 4 | 11 | 4+ | 3+ | 6.7 | | $>5 \times 10^5$ | pos | >3 | >10 |
| | 5 | 15 | 4+ | 4+ | 8.0 | | $>5 \times 10^5$ | pos | >3 | >10 |
| PHV913 | 1 | 0 | − | − | 0.0 | | $>5 \times 10^5$ | pos | 0.310 | 1.03 |
| genotype | 2 | 2 | − | − | 0.1 | | $>5 \times 10^5$ | pos | 0.330 | 1.10 |
| 2b | 3 | 7 | 2+ | − | 1.5 | | $>5 \times 10^5$ | pos | 0.867 | 2.89 |
| | 4 | 9 | 2+ | +/− | 1.7 | | $>5 \times 10^5$ | pos | 1.256 | 4.19 |
| PHV914 | 1 | 0 | − | − | 0.0 | | $>5 \times 10^5$ | pos | 0.292 | 0.97 |
| genotype | 2 | 5 | − | − | 0.0 | | $>5 \times 10^5$ | pos | 0.366 | 1.22 |
| 2b | 3 | 9 | − | − | 0.0 | | $>5 \times 10^5$ | pos | 0.307 | 1.02 |
| | 4 | 12 | − | − | 0.1 | | $>5 \times 10^5$ | pos | 0.325 | 1.08 |
| | 5 | 16 | 2+ | − | 1.2 | | $>5 \times 10^5$ | pos | 0.310 | 1.03 |
| | 6 | 19 | 2+ | − | 2.1 | | $>5 \times 10^5$ | pos | 0.323 | 1.08 |
| | 7 | 24 | 4+ | +/− | 4.5 | | $>5 \times 10^5$ | pos | 0.392 | 1.31 |
| | 8 | 30 | 4+ | 3+ | 6.8 | | $>5 \times 10^5$ | pos | 1.452 | 4.84 |
| | 9 | 33 | 4+ | 3+ | 7.6 | | $>5 \times 10^5$ | pos | 2.052 | 6.84 |
| PHV916 | 1 | 0 | − | − | 0.0 | | $3 \times 10^5$ | pos | 0.127 | 0.42 |
| genotype | 2 | 2 | − | − | 0.0 | | $>5 \times 10^5$ | pos | 0.297 | 0.99 |
| 2b | 3 | 7 | − | − | 0.0 | | $>5 \times 10^5$ | pos | 0.375 | 1.25 |
| | 4 | 9 | − | − | 0.0 | | $>5 \times 10^5$ | pos | 0.483 | 1.61 |
| | 5 | 16 | − | +/− | 0.3 | | $>5 \times 10^5$ | pos | 0.314 | 1.05 |
| | 6 | 19 | − | +/− | 1.1 | | $>5 \times 10^5$ | pos | 0.607 | 2.02 |
| | 7 | 23 | − | 3+ | 2.7 | | $4 \times 10^5$ | pos | 0.861 | 2.87 |
| | 8 | 28 | − | 3+ | 3.7 | | $2 \times 10^5$ | neg | 1.051 | 3.50 |
| PHV918 | 1 | 0 | − | − | 0.0 | HCV RNA | $>8 \times 10^5$ | pos | 0.272 | 0.91 |
| genotype | 2 | 2 | − | − | 0.0 | Roche | $>8 \times 10^5$ | pos | 0.544 | 1.81 |
| 1a | 3 | 7 | − | − | 0.0 | COBAS | $>8 \times 10^5$ | pos | 0.393 | 1.31 |
| | 4 | 9 | − | − | 0.0 | Amplicor | $>8 \times 10^5$ | pos | 0.660 | 2.20 |
| | 5 | 14 | − | − | 0.0 | PCR (BBI) | $>8 \times 10^5$ | pos | 0.441 | 1.47 |
| | 6 | 16 | +/− | − | 0.0 | IU/ml | $>8 \times 10^5$ | pos | 0.998 | 3.33 |
| | 7 | 24 | 3+ | − | 0.6 | | $>8 \times 10^5$ | pos | 0.368 | 1.23 |
| | 8 | 27 | 3+ | 1+ | 0.8 | | $>8 \times 10^5$ | pos | 0.627 | 2.09 |
| PHV920 | 1 | 0 | − | − | 0.0 | | $>8 \times 10^5$ | pos | 0.107 | 0.36 |
| genotype | 2 | 5 | − | − | 0.0 | | $>8 \times 10^5$ | pos | 0.891 | 2.97 |
| 1a | 3 | 7 | − | − | 0.0 | | $>8 \times 10^5$ | pos | 0.304 | 1.01 |
| | 4 | 13 | +/− | 1+ | 0.5 | | $>8 \times 10^5$ | pos | 2.292 | 7.64 |
| | 5 | 16 | 1+ | 3+ | 3.1 | | $>8 \times 10^5$ | pos | 2.840 | 9.47 |
| | 6 | 20 | 1+ | 3+ | 3.6 | | $3 \times 10^4$ | neg | 1.911 | 6.37 |

TABLE 4-continued

HCV antigen/antibody combination assay on BBI HCV seroconversion panels

| Seroconversion Panels | Days from 1st | anti-HCV RIBA 3.0 | | HCV 3.0 | HCV RNA | | HCV Ag (HCV core) | HCV Ag/Ab combination assay | |
|---|---|---|---|---|---|---|---|---|---|
| ID | Bleed | bleed | c22p | c33c | S/C | testing kit | quantity | Pos or (Neg) | OD | S/C |
| | | | From Panel Data Sheet | | | | | | | |
| | 7 | 26 | 1+ | 3+ | >5 | | $8 \times 10^4$ | neg | 1.637 | 5.46 |
| | 8 | 28 | 2+ | 4+ | >5 | | $2 \times 10^3$ | neg | 1.533 | 5.11 |
| | 9 | 33 | 2+ | 4+ | >5 | | BLD | neg | 2.374 | 7.91 |
| | | | negative plasma control-1 | | | | | | 0.016 | 0.05 |
| | | | negative plasma control-2 | | | | | | 0.019 | 0.06 |
| | | | negative plasma control-3 | | | | | | 0.011 | 0.04 |

TABLE 5

HCV antigen/antibody combination assay on ZeptoMetrix HCV seroconversion panels

| Seroconversion Panels | Days from 1st | anti-HCV RIBA 3.0 | | HCV 3.0 | HCV RNA | | HCV Ag (HCV core) | HCV Ag/Ab combination assay | |
|---|---|---|---|---|---|---|---|---|---|
| ID | Bleed | bleed | c22p | c33c | S/C | testing kit | quantity | Pos or (Neg) | OD | S/C |
| | | | From Panel Data Sheet | | | | | | | |
| 6212 | 1 | 0 | − | − | 0.00 | CHIRON | $1.88 \times 10^6$ | pos | 0.086 | 0.29 |
| | 2 | 12 | − | +/− | 0.15 | HCV RNA | $2.21 \times 10^5$ | neg | 1.965 | 6.55 |
| | 3 | 14 | − | +/− | 0.30 | Copies/mL | <200,000 | neg | 2.503 | 8.34 |
| | 4 | 23 | − | 1+ | 1.49 | | $2.27 \times 10^5$ | neg | >3 | >10 |
| | 5 | 26 | − | 1+ | 1.87 | | $2.03 \times 10^5$ | neg | >3 | >10 |
| | 6 | 32 | − | 1+ | 2.37 | | <200,000 | neg | >3 | >10 |
| | 7 | 37 | − | 1+ | 2.46 | | $3.91 \times 10^5$ | neg | >3 | >10 |
| | 8 | 53 | − | 4+ | 4.13 | | $4.66 \times 10^5$ | neg | >3 | >10 |
| | 9 | 55 | − | 4+ | 4.13 | | $3.57 \times 10^5$ | neg | >3 | >10 |
| 6215 | 1 | 0 | − | − | 0.00 | CHIRON | $>120 \times 10^6$ | pos | 0.898 | 2.99 |
| | 2 | 3 | − | − | 0.01 | HCV RNA | $104 \times 10^6$ | pos | 0.952 | 3.17 |
| | 3 | 10 | − | − | 0.02 | (bDNA) | $58 \times 10^6$ | pos | 0.456 | 1.52 |
| | 4 | 20 | 4+ | +/− | 4.66 | (copies/ml) | $48 \times 10^6$ | pos | 2.321 | 7.74 |
| 6225 | 10 | 35 | − | − | 0.00 | CHIRON | <0.2 | neg | 0.034 | 0.11 |
| | 11 | 39 | − | − | 0.00 | bDNA | <0.2 | neg | 0.021 | 0.07 |
| | 12 | 45 | − | − | 0.00 | (MEq/mL) | 27.02 | pos | 0.266 | 0.89 |
| | 13 | 47 | − | − | 0.00 | | 98.84 | pos | 0.678 | 2.26 |
| | 14 | 52 | − | − | 0.00 | | 77.79 | pos | 0.627 | 2.09 |
| | 15 | 56 | − | − | 0.01 | | 54.71 | pos | 0.545 | 1.82 |
| | 16 | 60 | − | − | 0.00 | | >120 | pos | 1.027 | 3.42 |
| | 17 | 72 | − | − | 0.07 | | 9.37 | pos | 0.635 | 2.12 |
| | 18 | 77 | − | 1+ | 1.73 | | 4.97 | pos | 1.380 | 4.60 |
| | 19 | 79 | − | 1+ | 2.11 | | 3.24 | pos | 1.400 | 4.67 |
| 6229 | 1 | 0 | − | − | 0.01 | | 52.19 | pos | 0.490 | 1.63 |
| | 2 | 3 | − | − | 0.01 | | 55.83 | pos | 0.528 | 1.76 |
| | 3 | 7 | − | − | 0.01 | | 55.53 | pos | 0.452 | 1.51 |
| | 4 | 10 | − | − | 0.01 | | 94.76 | pos | 0.823 | 2.74 |
| | 5 | 18 | − | − | 0.53 | | 31.88 | pos | 1.346 | 4.49 |
| | 6 | 21 | − | +/− | 1.06 | | 69.85 | pos | 1.636 | 5.45 |
| | 7 | 25 | +/− | 1+ | 1.71 | | 51.02 | pos | 1.594 | 5.31 |
| | 8 | 29 | +/− | 3+ | 4.07 | | 43.89 | pos | 2.590 | 8.63 |
| 9041 | 1 | 0 | − | − | 0.00 | CHIRON | <0.2 | neg | 0.044 | 0.15 |
| | 2 | 24 | − | − | 0.01 | HCV RNA | 15.78 | pos | 0.125 | 0.42 |
| | 3 | 27 | − | − | 0.01 | bDNA 2.0 | 63.72 | pos | 0.603 | 2.01 |
| | 4 | 31 | − | − | 0.01 | (MEq/mL), * | >120 | pos | 1.106 | 3.69 |
| | 5 | 62 | +/− | 4+ | 7.30 | one Mega | 72.27 | pos | 2.924 | 9.75 |
| | 6 | 64 | +/− | 4+ | 8.03 | Equivalent/mL | 66.27 | pos | >3 | >10 |
| | 7 | 69 | 1+ | 4+ | 8.20 | (MEq/mL) | 21.80 | pos | >3 | >10 |
| | 8 | 71 | 3+ | 4+ | 8.78 | is ≈ 1 million | 11.24 | pos | >3 | >10 |
| 9044 | 1 | 0 | − | − | 0.00 | equivalents | 105.90 | pos | 0.652 | 2.17 |
| | 2 | 4 | − | − | 0.01 | of HCV RNA. | 52.71 | pos | 0.496 | 1.65 |
| | 3 | 17 | − | − | 0.00 | | 77.18 | pos | 0.722 | 2.41 |
| | 4 | 21 | − | +/− | 0.69 | | 71.52 | pos | 1.089 | 3.63 |

TABLE 5-continued

HCV antigen/antibody combination assay on ZeptoMetrix HCV seroconversion panels

| Seroconversion Panels ID | Bleed | Days from 1st bleed | anti-HCV RIBA 3.0 c22p | anti-HCV RIBA 3.0 c33c | HCV 3.0 S/C | HCV RNA testing kit | HCV RNA quantity | HCV Ag (HCV core) Pos or (Neg) | HCV Ag/Ab combination assay OD | HCV Ag/Ab combination assay S/C |
|---|---|---|---|---|---|---|---|---|---|---|
| | 5 | 25 | − | 2+ | 3.70 | | 72.82 | pos | 1.147 | 3.82 |
| | 6 | 29 | − | 3+ | 4.51 | | 48.83 | pos | 0.855 | 2.85 |
| 9045 | 1 | 0 | − | − | 0.00 | | 17.73 | pos | 0.361 | 1.20 |
| | 2 | 2 | − | − | 0.00 | | 16.42 | pos | 0.321 | 1.07 |
| | 3 | 7 | − | − | 0.00 | | 36.19 | pos | 0.395 | 1.32 |
| | 4 | 9 | − | − | 0.01 | | 38.07 | pos | 0.557 | 1.86 |
| | 5 | 26 | − | − | 0.00 | | 44.86 | pos | 0.389 | 1.30 |
| | 6 | 32 | − | − | 0.04 | | 17.78 | pos | 0.302 | 1.01 |
| | 7 | 37 | − | 1+ | 2.61 | | 18.36 | pos | 1.314 | 4.38 |
| | 8 | 41 | − | 2+ | 3.51 | | 2.32 | pos | 1.043 | 3.48 |
| 9047 | 1 | 0 | − | − | 0.10 | | 65.95 | pos | 0.474 | 1.58 |
| | 2 | 2 | − | − | 0.12 | | 81.76 | pos | 0.517 | 1.72 |
| | 3 | 10 | − | − | 0.09 | | 54.85 | pos | 0.368 | 1.23 |
| | 4 | 12 | − | − | 0.05 | | 64.03 | pos | 0.501 | 1.67 |
| | 5 | 19 | − | − | 0.10 | | 55.45 | pos | 0.346 | 1.15 |
| | 6 | 21 | − | − | 0.09 | | 42.97 | pos | 0.334 | 1.11 |
| | 7 | 28 | − | 2+ | 1.51 | | 9.13 | pos | 2.921 | 9.74 |
| | 8 | 30 | − | 4+ | 3.92 | | 26.58 | pos | 2.992 | 9.97 |
| | 9 | 35 | − | 4+ | 7.36 | | 22.77 | pos | >3 | >10 |
| | 10 | 37 | +/− | 4+ | 6.77 | | nd | pos | >3 | >10 |
| 9054 | 7 | 52 | − | − | 0.00 | | <0.2 | neg | 0.040 | 0.13 |
| | 8 | 74 | +/− | − | 0.00 | | 86.79 | pos | 0.555 | 1.85 |
| | 9 | 77 | 1+ | +/− | 0.14 | | 86.75 | pos | 0.532 | 1.77 |
| | 10 | 82 | 2+ | 1+ | 3.16 | | 59.14 | pos | >3 | >10 |
| 9058 | 1 | 0 | +/− | − | 0.07 | | 90.58 | pos | 0.762 | 2.54 |
| | 2 | 3 | +/− | − | 0.08 | | 85.34 | pos | 0.764 | 2.55 |
| | 3 | 7 | + | +/− | 0.15 | | 37.64 | pos | 0.487 | 1.62 |
| | 4 | 10 | 1+ | 1+ | 0.66 | | 48.33 | pos | 0.930 | 3.10 |
| | 5 | 14 | 2+ | 1+ | 3.16 | | 29.46 | pos | 1.209 | 4.03 |
| | | | | | negative plasma control-1 | | | | 0.016 | 0.05 |
| | | | | | negative plasma control-2 | | | | 0.019 | 0.06 |
| | | | | | negative plasma control-3 | | | | 0.011 | 0.04 |

What is claimed is:

1. An immunoassay for simultaneously detecting HCV antigens and antibodies in a sample, comprising:
   providing a non-ionic detergent Lauryldimethylamine N-oxide (LDAO), a first pair of a capture antigen and a detection antigen, a first pair of a capture antibody and a conjugate antibody, wherein said capture antigen and said detection antigen both comprise a first peptide fragment of a first HCV protein, said capture antibody and said conjugate antibody specifically bind to a second HCV protein, and said detection antigen and said conjugate antibody comprise one and same signal generating means;
   contacting said sample in the presence of said detergent with said capture antigen, said detection antigen, said capture antibody and said conjugate antibody, to form a sandwich complex between said capture antigen, said detection antigen, and an anti-HCV antibody present in said sample, and a complex between said capture antibody, said conjugate antibody, and an HCV antigen present in said sample; and
   measuring a signal generated from said signal-generating means as a result of the formation of said complexes, thereby simultaneously detecting HCV antigens and antibodies in said sample.

2. The immunoassay of claim 1, wherein said first HCV protein and second HCV protein are independently selected from the group consisting of the core antigen, E1, E2, NS2, NS3, NS4, and NS5.

3. The immunoassay of claim 1, wherein said first HCV protein and said second HCV protein are the same, and said capture antibody and said conjugate antibody bind to a region of said second HCV protein outside of said first peptide fragment.

4. The immunoassay of claim 3, wherein said first HCV protein and said second HCV protein are both the HCV core antigen.

5. The immunoassay of claim 1, wherein a second pair of a capture antigen and a detection antigen is provided, wherein said capture antigen and said detection antigen of the second pair both comprise a second peptide fragment of an HCV protein, wherein said second peptide fragment is different from said first peptide fragment.

6. The immunoassay of claim 1, wherein said capture antibody in said first pair comprises two or more antibodies.

7. The immunoassay of claim 1, wherein a second pair of a capture antibody and a conjugate antibody is provided, wherein said capture antibody and said conjugate antibody in said second pair specifically bind to said second HCV protein or a different HCV protein.

8. The immunoassay of claim 1, wherein said capture antigen and said capture antibody are attached to a solid phase.

9. The method of claim 1, wherein LDAO is present in the range of 0.1 to 2.0%.

10. The method of claim 9, wherein LDAO is present in the range of 0.3 to 1.0%.